(12) United States Patent
Azzolini

(10) Patent No.: US 6,712,786 B2
(45) Date of Patent: Mar. 30, 2004

(54) SINGLE-USE PREASSEMBLED MEDICAL DEVICE FOR ADMINISTERING AT LEAST TWO DRUGS IN PRESET PROPORTIONS TO PATIENTS

(75) Inventor: Graziano Azzolini, Cavezzo (IT)

(73) Assignee: Sidam di Azzolini Graziano E C. S.a.s. (IT)

( * ) Notice: Subject to any disclaimer, the term of this patent is extended or adjusted under 35 U.S.C. 154(b) by 57 days.

(21) Appl. No.: 09/877,561

(22) Filed: Jun. 8, 2001

(65) Prior Publication Data

US 2001/0051791 A1 Dec. 13, 2001

(30) Foreign Application Priority Data

Jun. 9, 2000 (IT) .................... MO2000A0124

(51) Int. Cl.[7] .................... A61M 5/14; A61M 37/00; A61M 5/00; A61M 25/00; A61B 19/00
(52) U.S. Cl. .................... 604/80; 604/83; 604/131; 604/256; 604/284; 604/408; 604/411
(58) Field of Search .................... 604/79, 80, 82, 604/83, 122, 131, 151, 153, 191, 246, 251, 256, 284, 408–416

(56) References Cited

U.S. PATENT DOCUMENTS

| 3,991,912 A | | 11/1976 | Soto |
|---|---|---|---|
| 4,201,406 A | | 5/1980 | Dennehey et al. |
| 4,944,726 A | | 7/1990 | Hilal et al. |
| 5,531,733 A | * | 7/1996 | Scarrow .................... 604/411 |
| 5,653,698 A | * | 8/1997 | Niedospial et al. .......... 604/537 |
| 5,935,100 A | * | 8/1999 | Myers .......................... 604/81 |
| 5,968,014 A | * | 10/1999 | Neftel et al. ................. 604/151 |
| 5,971,972 A | | 10/1999 | Rosenbaum |
| 6,102,889 A | * | 8/2000 | Wijnhoud .................... 604/80 |

FOREIGN PATENT DOCUMENTS

| DE | 19723014 A1 | 12/1998 |
|---|---|---|
| WO | WO98/47559 A1 | 10/1998 |
| WO | WO99/59522 A1 | 11/1999 |

OTHER PUBLICATIONS

Translation of DE 197 23 014 A1*
European Search Report and Annex to the European Search Report on European Patent Application No. EP 01112951: Jul. 18, 2002, 3 pages, The Hague.

* cited by examiner

Primary Examiner—Brian L. Casler
Assistant Examiner—Mark K. Han
(74) Attorney, Agent, or Firm—Wolf, Greenfield & Sacks P.C.

(57) ABSTRACT

A single-use preassembled medical device for administering at least two drugs in preset proportions to patients, comprising at least one pair of independent injectors and at least one pair of piercing couplings for corresponding bottles containing the drugs which are reciprocally connected by corresponding tubes which lead into a single tube for infusion to a patient; at least one of the piercing couplings is of a conventional type and the second one is of a dedicated type, forming a conveniently provided small cup-shaped receptacle for the precision insertion of the neck of a bottle of a preset drug whose dimensions are likewise correspondingly smaller than those of a normal bottle.

11 Claims, 4 Drawing Sheets

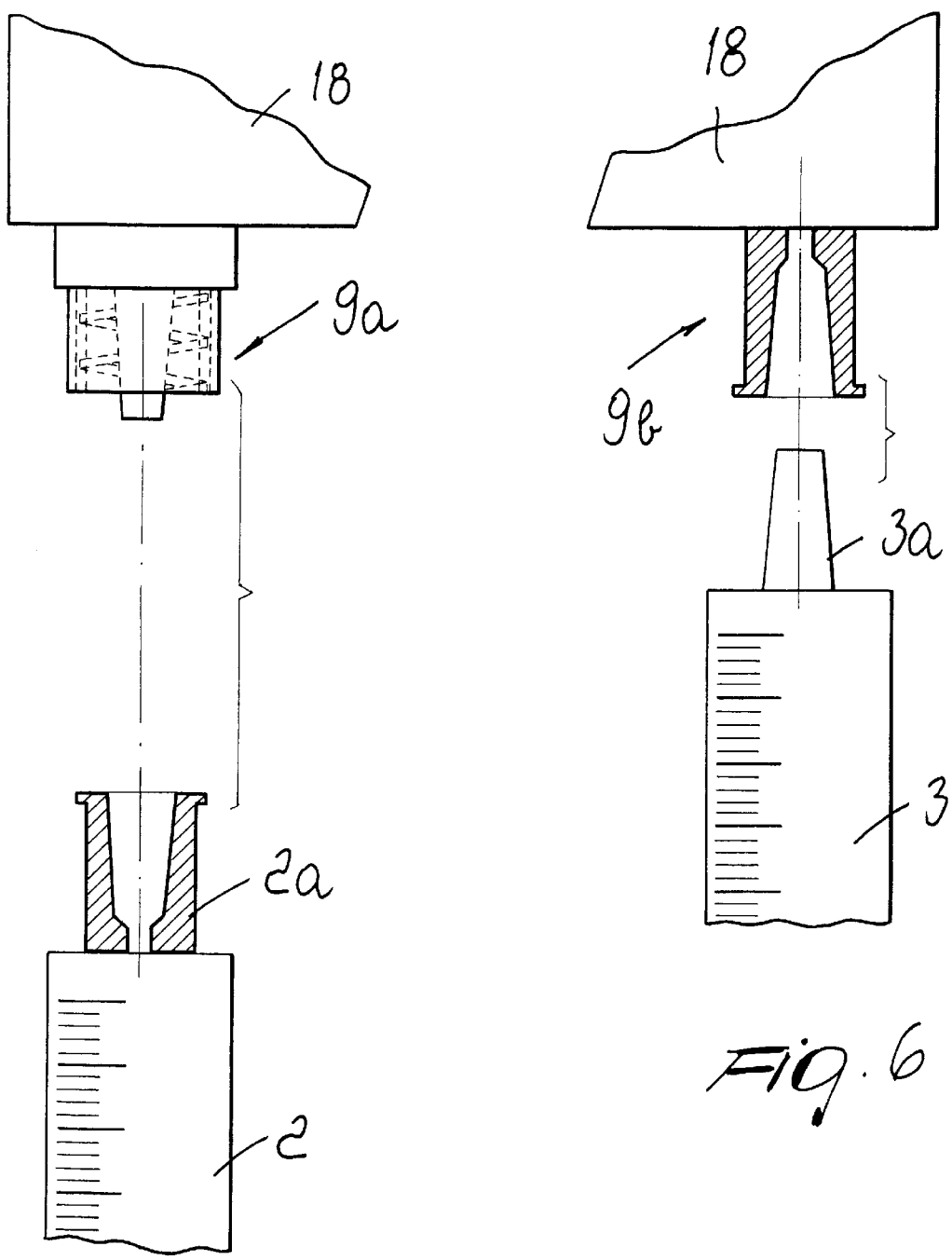

SINGLE-USE PREASSEMBLED MEDICAL DEVICE FOR ADMINISTERING AT LEAST TWO DRUGS IN PRESET PROPORTIONS TO PATIENTS

CROSS-REFERENCE TO RELATED APPLICATIONS

This application claims priority to Italian Application Serial No. MO2000A000124 filed Jun. 9, 2000, the disclosure of which is incorporated herein by reference.

BACKGROUND OF THE INVENTION

The present invention relates to a single-use preassembled medical device for administering at least two drugs in preset proportions to patients.

Preassembled single-use devices have long been known and used in the medical field and are packaged in sealed envelopes in order to maintain the sterility acquired by said devices after a sterilization treatment to which they are subjected after packaging.

When such devices are used, their particular structural characteristics must be able to preserve as much as possible the sterility characteristics of the entire device throughout administration to the patient.

Among such devices, some are used in particular administrations of a plurality of drugs in proportions which are predefined by doctors and which, in order to avoid endangering the patients, must keep the proportions strictly invariant.

A specific example of this type of device is the line of tubing and couplings used to perform angiographies by magnetic resonance, or magnetic-resonance diagnostic tests, in which it is necessary to use at least two injection syringes which are driven by a convenient presettable automatic device (injector); in a first step, each one of the syringes aspirates from a respective bottle containing contrast liquid for one syringe and physiological solution for the other syringe in calculated amounts; in a second step, the syringes inject the liquid and the solution into the patient by means of convenient tubes which are part of the single-use device.

Such device requires maximum attention on the part of assigned operators during the handling required to provide the several connections, since in addition to preventing external contaminations it is absolutely indispensable to avoid errors in mutually connecting the components due to evident patient safety reasons.

Currently, the devices used to perform these therapies have no barriers which can practically avoid the possibility of operator error in connecting both the ends of the tubes which enter the bottles with convenient piercing elements and the opposite ends which lead into the combined manifold tube leading to the syringes of the injector.

SUMMARY OF THE INVENTION

The aim of the present invention is to solve the above-noted drawbacks of the prior art by providing a single-use preassembled medical device for administering at least two drugs in preset proportions to patients, which first of all ensures maximum safety in the administration by preventing, with absolute safety, the operators from performing incorrect connections between the connection tubes, between the bottles that contain the drugs or the like, and the patient, and of the means adapted to administer the drugs, i.e. the syringes of the injector, and further ensures the sterility of the device and of the bottles connected thereto and of their contents, since once they are opened they are subject to likely contaminations, with the easily imaginable severe consequences for the patients after the first withdrawal.

This aim and other objects which will become better apparent hereinafter are achieved by a single-use preassembled medical device for administering at least two drugs in preset proportions to patients, comprising at least one pair of independent injector means and at least one pair of piercing couplings for corresponding bottles containing said drugs which are mutually connected by means of corresponding tubes leading into a single tube for infusion to a patient, characterized in that at least one of said piercing couplings forms a small cup-shaped receptacle for precision insertion of the neck of a bottle of a preset drug having correspondingly small dimensions.

BRIEF DESCRIPTION OF THE DRAWINGS

Further characteristics and advantages of the present invention will become better apparent from the description of a preferred embodiment of a single-use preassembled medical device for administering at least two drugs in preset proportions to patients, illustrated only by way of non-limitative example in the accompanying drawings, wherein:

FIGS. 5 and 6 are respectively detail views of the couplings provided with mutually incompatible shapes of the injector means with the preassembled and single-use device according to the invention.

DESCRIPTION OF THE PREFERRED EMBODIMENTS

Figure 1:
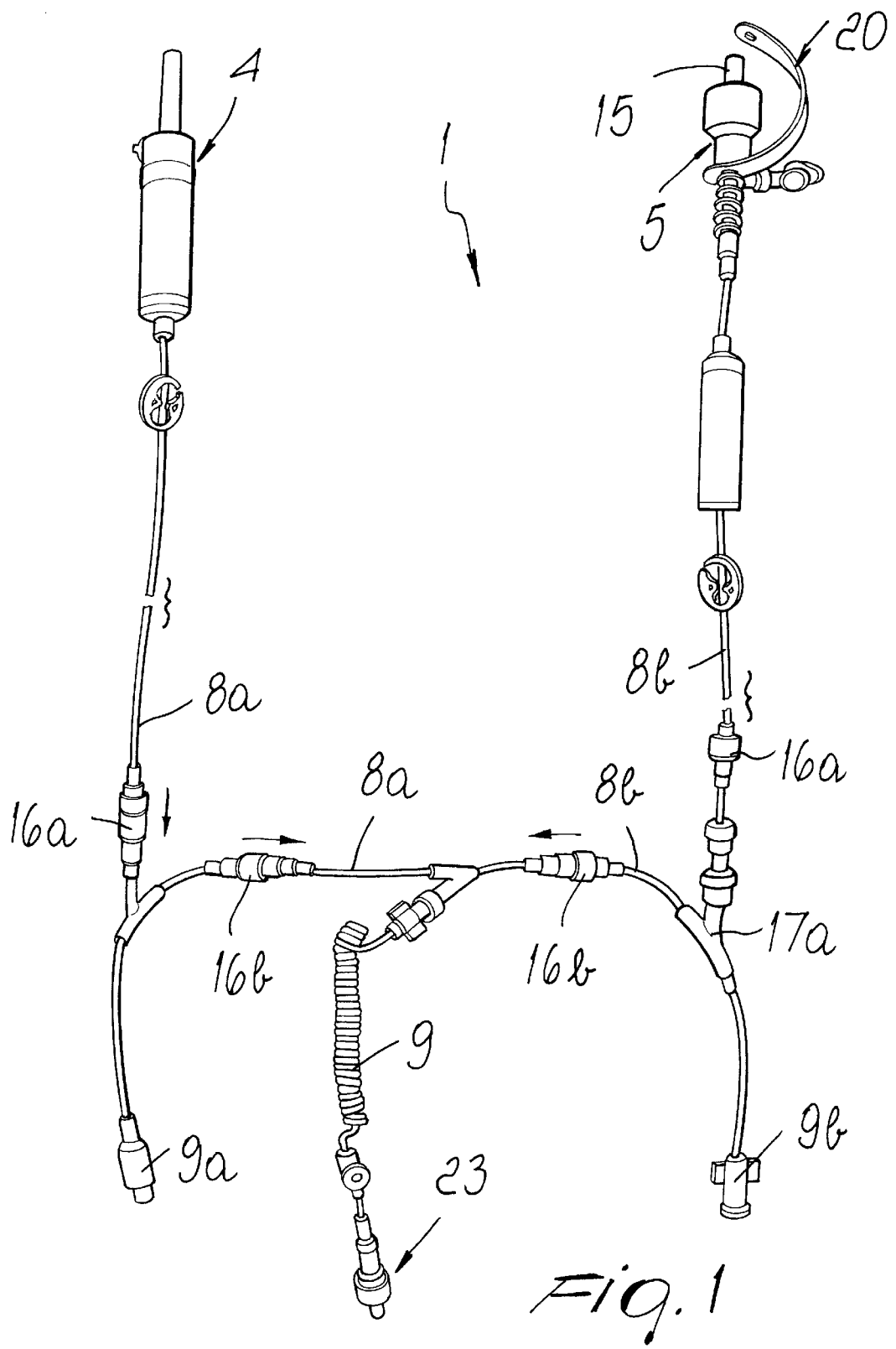
FIG. 1 is a view of the single-used preassembled device according to the invention, in a first embodiment.
Figure 2:
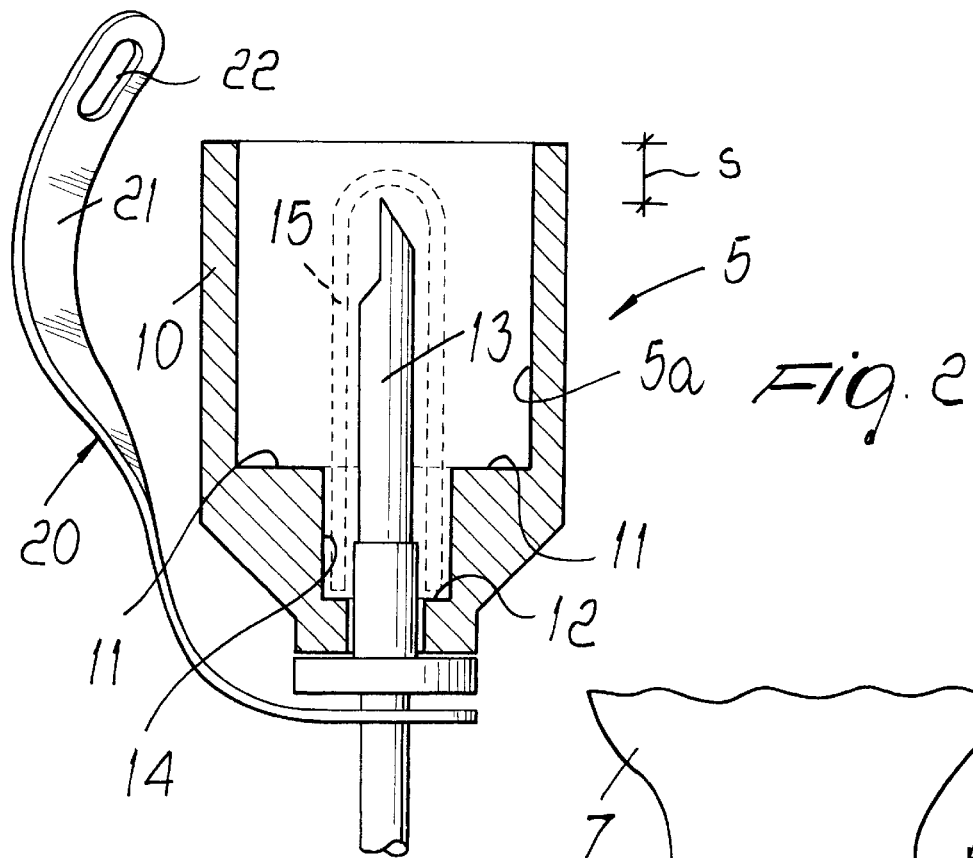
FIG. 2 is an enlarged-scale longitudinal sectional detail view of a dedicated-type piercing coupling.
Figure 3:
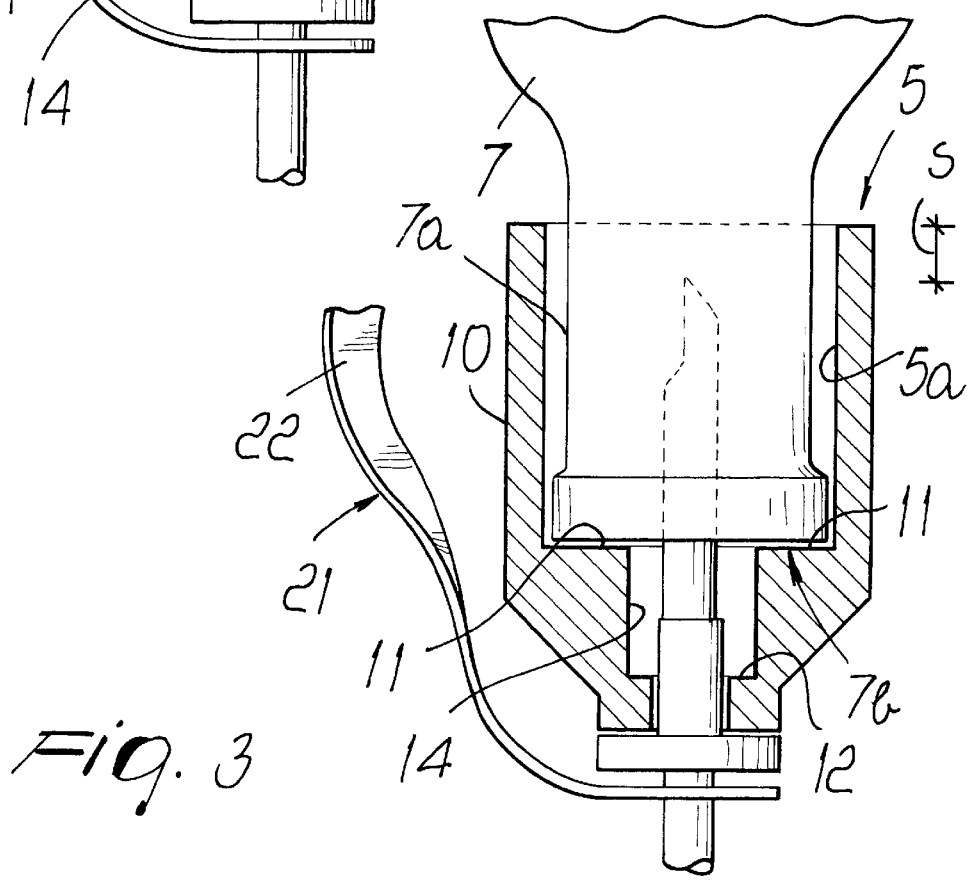
FIG. 3 is another sectional view of the dedicated-type piercing coupling, in which the neck of a corresponding smaller bottle is inserted.
Figure 4:
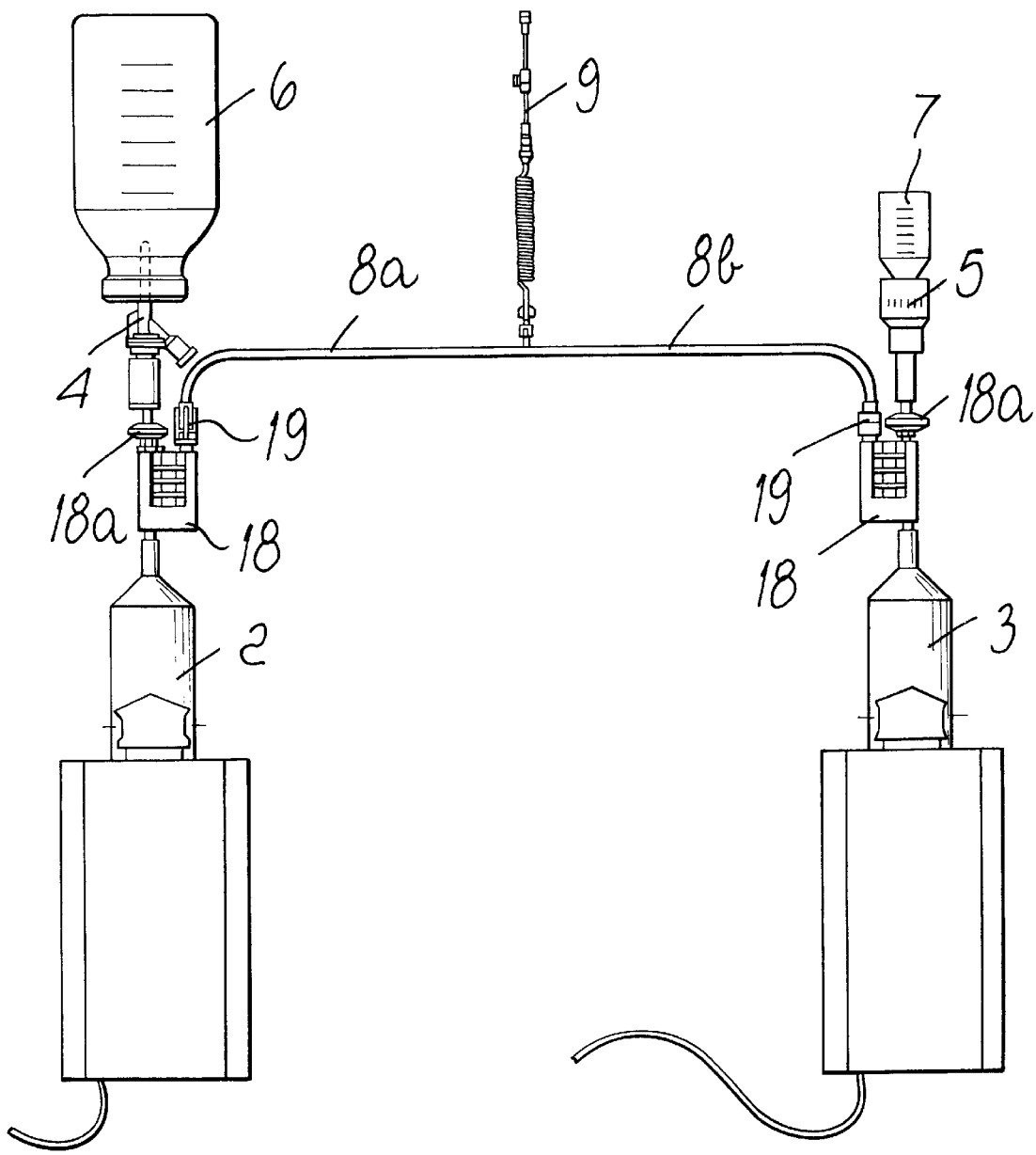
FIG. 4 is a view of a second embodiment of the preassembled single-use device according to the invention.

With reference to the figures, the reference numeral 1 designates a single-use preassembled medical device for administering at least two drugs in preset proportions to patients, which comprises at least one pair of independent injector means 2 and 3, each of which being constituted in practice by a syringe, and at least one pair of piercing couplings 4 and 5 for corresponding bottles 6 and 7 which contain said drugs.

The syringes 2 and 3, having respectively couplings of the female type 2a and of the male type 3a with Luer-type taper at their inlet/outlet, and the piercing couplings 4 and 5 are connected one another by means of two branches of corresponding tubes, designated respectively by the reference numerals 8a and 8b, which lead into a single tube 9 for infusion into a patient.

Of the two piercing couplings 4 and 5, one, e.g. the coupling 4, is of the conventional type, while the second one 5 is of a so-called "dedicated" type, i.e. it is shaped like a small cup-like receptacle 5a in order to receive the precision insertion of the neck 7a of the bottle 7 which contains a preset drug, the bottle 7 correspondingly having smaller dimensions directly from its packaging.

The couplings 9a and 9b between the tubes 8a and 8b and the injector means 2 and 3 are respectively of the male type and of the female type, or vice versa, and are in any case such that they are incompatible one another and therefore cannot be swapped even inadvertently with the couplings 2a and 3a; said couplings 9a and 9b also are commonly known as "Luer-Loks" and are in any case respectively of the female type and of the male type, as mentioned.

The second coupling 5 of the dedicated type is constituted by a cylindrical body 10 which centrally forms the already-mentioned receptacle 5a and is provided, on its bottom, with shoulders 11 for the abutment of the mouth 7b of the smaller bottle 7; a conventional stem-like piercing element 13 protrudes outward at right angles from the center of the base 12 of the receptacle 5a and is shorter, by an extent S, than the overall height of the walls of the receptacle 5a.

A circular recess 14 remains between the shoulders 11 and the bottom 12 and is adapted to receive the base of a removable cap 15 for covering the piercing element 13 in the inactive condition.

In order to prevent the return of the flow of the drugs from the syringes 2 and 3 to the bottles 6 and 7 during delivery, i.e. during aspiration of the blood of the patient during the loading of said syringes from the bottles 6 and 7, on each branch 8a and 8b of said tubes unidirectional valve means are provided, i.e. in greater detail, each branch is fitted with at least two unidirectional valve means 16a and 16b; the first valve means 16a is located on a segment which lies between a piercing coupling and a point 17a for merging towards the corresponding injector means, and the second valve means 16b is located between said merging point 17a and the single tube 9.

In a preferred embodiment of the invention, the two piercing couplings 4 and 5 and each corresponding pair of unidirectional valve means 16a and 16b are combined into a single monolithic element 18 which is provided with a direct coupling to the corresponding injector means and with at least one outlet 19 for connection to the single infusion tube 9; the monolithic element 18 is shaped anatomically in order to be easily gripped and handled by operators during connection and disconnection with respect to the syringes 2 and 3 and is self-supporting so as to directly support the weight of the corresponding bottle, therefore without requiring any supporting element, which is awkward and bulky.

The inlet of each monolithic element 18 is further protected by means of a filter 18a, and each direct coupling of each monolithic element 18 is alternatively of the male type 9a or of the female type 9b, correspondingly for each one, in order to couple to the corresponding couplings 2a and 3a of the syringes 2 and 3.

The second piercing coupling 5 of the dedicated type is provided with means 20 for engaging a conventional supporting element which are constituted by at least one flexible strap 21 in which one end is rigidly coupled to the piercing coupling 5 and the opposite free end is affected by a slot 22 for the passage of a corresponding hook of said conventional supporting element.

The operation of the device according to the invention is as follows: when a health operator has to administer to a patient a particular drug formed by two components which are stored in convenient containment bottles 6 and 7, he inserts as usual the corresponding piercing coupling in the elastomeric closure of the containers.

In particular, at least one of the bottles, in this case the one designated by the reference numeral 7 in the drawings, is usually smaller, since it is adapted to contain a highly concentrated substance to be diluted, while the bottle 6 has normal dimensions and contains the conveniently provided diluent (physiological solution) for such substance.

During the insertion maneuver, after removing the cap 15, the piercing coupling 5 is adapted to receive only the small bottle 7, since the neck 7a of the small bottle is the only one that can be inserted in the receptacle 5a; in this manner, it becomes impossible for the operator to accidentally swap the bottles 6 and 7, since the first normal-size one would not enter the receptacle 5a.

It is noted that the limited length of the stem-like piercing element 13 with respect to the walls of the receptacle 5a, together with the abutment shoulders 11 for the mouth 7b, allow to position the bottle 7 in the coupling 5 so that it can be emptied completely, the penetration of said stem-like piercing element 13 in the neck 7a being limited to a predefined level; in this manner, the contents of said bottle 7, which are usually expensive, are used optimally.

After completing the first connection step, the operator completes the process by inserting the male coupling 9a and the female coupling 9b on the female and male Luer-taper mouths 2a and 3a of the corresponding syringes 2 and 3; these force the operator to comply with the connections as provided, with no possibility of swapping the couplings 9a and 9b with the syringes 2 and 3.

After the connections have been completed, the syringes 2 and 3, actuated by a convenient programmable actuation machine, aspirate during a first step, through the branches 8a and 8b, the amounts of the drugs prescribed for performing the therapy; in the second step, they inject the aspirated volumes in guided proportion into the patient by means of the infusion tube 9.

In order to prevent accidental reverse flows of drugs, the pairs of unidirectional valves 16a and 16b are arranged on both branches 8a and 8b; the valve 16a in practice prevents the reverse flow of the drug beyond each merging point 17a when the corresponding syringe is in the injection step, while the valve 16b prevents aspiration from the patient through the line 9, which is in any case rendered impossible by an additional unidirectional valve 23 arranged at the end of the line which is directed towards the patient, and most of all prevents aspiration between the syringes 2 and 3, i.e. between the cross-connected bottles.

In a second embodiment of the preassembled medical device 1, in order to allow more comfortable and rapid use on the part of health operators, the piercing couplings 4 and 5 and the pairs of unidirectional valves 16a and 16b are combined into a single corresponding monolithic element 18 which can constitute an anatomical handling grip portion.

A filter 18a is fitted between each inlet of the monolithic elements 18 and the corresponding piercing coupling; the filter is adapted to retain any elastomeric residues generated during the piercing of the closures of the bottles 6 and 7; moreover, for each element 18 an outlet 19 is provided being connectable to the infusion tube 9.

The monolithic elements 18 for connection to the respective syringes 2 and 3 also have mutually different couplings of the male and female type, all having a Luer-type taper, so as to avoid any accidental swapping.

In practice it has been found that the described invention achieves the intended aim and objects.

The invention thus conceived is susceptible of numerous modifications and variations, all of which are within the scope of the appended claims.

All the details may further be replaced with other technically equivalent ones.

In practice, the materials used, as well as the shapes and the dimensions, may be any according to requirements without thereby abandoning the scope of the protection of the appended claims.

The disclosures in Italian Patent Application No. MO2000A000124 from which this application claims priority are incorporated herein by reference.

What is claimed is:

1. A single-use preassembled medical device for administering at least two drugs in preset proportions to patients, comprising at least one pair of independent injector means and at least one pair of piercing couplings for corresponding bottles containing said drugs which are connectable by means of corresponding tubes which lead into a single tube for infusion to a patient, wherein at least one of said piercing couplings forms a small cup-shaped receptacle for precision insertion of a neck of a bottle of a preset drug having correspondingly small dimensions and wherein unidirectional valve means are mounted on each branch of said tubes of each bottle, wherein one of the couplings between said tubes and said injector means is of a male type and another one is of a female type, said couplings being incompatible.

2. The device according to claim 1, wherein said at least one of said piercing couplings is constituted by a cylindrical body which centrally forms said receptacle and has, on a bottom thereof, shoulders for abutment of a mouth of said corresponding bottle, a stem-like piercing element protruding outward at right angles from a center of a base of said receptacle.

3. The device according to claim 2, wherein a circular recess is formed between said shoulders and said bottom and is adapted to receive the base of a removable cap for covering said piercing element in the inactive condition.

4. The device according to claim 2, wherein said stem-like piercing element is shorter than an overall height of the walls that form said receptacle.

5. The device according to claim 1, wherein at least two unidirectional valve means are fitted on each branch of said tubes, a first valve means being fitted in a segment which lies between a piercing coupling and a merging point towards the corresponding injector means and a second valve means being fitted between said merging point and said single tube for infusion to a patient.

6. The device according to claim 1, wherein each one of said injector means is constituted by a syringe which can be actuated automatically from a first aspiration step to a second injection step.

7. The device according to claim 5, wherein each piercing coupling and each corresponding pair of unidirectional valve means are combined into a monolithic element which is provided with a direct coupling to a corresponding injector means and with at least one outlet for connection to said single infusion tube.

8. The device according to claim 7, wherein said monolithic element is anatomically shaped to allow easy grip for handling by operators.

9. The device according to claim 7, wherein at least said one piercing coupling is provided with means for engaging a supporting element.

10. The device according to claim 1, wherein at least said one piercing coupling is provided with means for engaging a supporting element.

11. The device according to claim 10, wherein said engagement means are constituted by at least one flexible strap which has an end rigidly coupled to said piercing coupling and an opposite end which is free and affected by a slot for insertion of a corresponding hook of said supporting element.

* * * * *